United States Patent [19] [11] 4,233,559
Hoberg et al. [45] Nov. 11, 1980

[54] QUICKLY PERFORMED MEASURING METHOD FOR ASCERTAINING THE CONCENTRATION OF THE POLAR COMPONENTS IN A MATERIAL OTHERWISE MAINLY NON-POLAR

[75] Inventors: Heinz Hoberg, Aachen-Laurensberg; Albert Klein, Walhorn-Belgien, both of Fed. Rep. of Germany

[73] Assignee: Bergwerksverband GmbH, Essen, Fed. Rep. of Germany

[21] Appl. No.: 16,063

[22] Filed: Feb. 28, 1979

[30] Foreign Application Priority Data

Mar. 1, 1978 [DE] Fed. Rep. of Germany ....... 2808739

[51] Int. Cl.$^3$ ............................................. G01R 27/04
[52] U.S. Cl. ............................................. 324/58.5 A
[58] Field of Search .............. 324/58.5 A, 58 A, 58 R

[56] References Cited

U.S. PATENT DOCUMENTS

| 2,774,876 | 12/1956 | Dicke | 324/58.5 A |
| 3,093,825 | 6/1963 | Allen | 324/58 A X |
| 3,155,898 | 11/1964 | Chope | 324/58.5 A |
| 3,448,380 | 6/1969 | Harrington | 324/58.5 A |
| 3,538,434 | 11/1970 | Brown et al. | 324/58.5 A |

Primary Examiner—Stanley T. Krawczewicz
Attorney, Agent, or Firm—Michael J. Striker

[57] ABSTRACT

Conventionally, the concentration of a polar component in an otherwise non-polar or negligibly polar material, e.g., water content in pourable coal, is ascertained by measuring the attenuation of electromagnetic waves transmitted through a layer-thin sample of the material, the waves having a frequency as near as possible to the maximum-dipole-relaxation-loss frequency $f_o$, in order to maximize the power-loss effect of the transmitted waves, this being directly attributable to the polar component, and thereby serving to accentuate the effect of the polar component in the measurement signal. The present invention operates at lower frequencies, associated with low dipole-relaxation power-loss, and measures the time delay of the thusly transmitted waves, achieving an unexpected degree of temperature-independence in the measurement signal obtained, and simultaneously, because the power attenuation per unit thickness of the sample is so greatly decreased, making possible the use of samples of unprecedently great thickness, e.g., 1-meter-thick masonry walls whose water content is to be ascertained, compared to the 0.1-meter or 0.2-meter-thick samples to which such techniques have hitherto been limited.

16 Claims, No Drawings

QUICKLY PERFORMED MEASURING METHOD FOR ASCERTAINING THE CONCENTRATION OF THE POLAR COMPONENTS IN A MATERIAL OTHERWISE MAINLY NON-POLAR

BACKGROUND OF THE INVENTION

The present invention concerns quickly performed measuring methods of the type employed to ascertain the concentration of one or more polar components in a material otherwise mainly comprised of one or more non-polar or only negligibly polar components. Methods of the type here in question involve the measurement of electromagnetic waves transmitted through the material of interest.

Determining the concentration of polar components in otherwise mainly non-polar or only slightly polar materials extends into an enormous variety of practical applications and fields of technology, as revealed by the last several decades of research and development in this particular area. Techniques for making this type of determination are desired both for situations in which the polar and non-polar components of the material are present in the same state of matter and also for situations in which such components are present in different states of matter. In general, the material to be analyzed with respect to concentration of polar components may be a gas, a liquid, a solid, or a combination thereof.

As well known, it can be particularly difficult to perform such concentration measurements upon the polar components in pourable bulk materials, such as coal, because the magnitude of the measurement signal yielded by conventional techniques in general will exhibit a high degree of dependence upon the size of the constituent particles, grains or chunks of such pourable bulk material. When such bulk materials are involved, measurement of polar-component concentration is most usually performed to ascertain the water or moisture content of the material. Lately, when applications such as this are involved, increasing interest has been exhibited by the art in the use of microwave waveguide technology as the means for establishing the requisite electromagnetic-wave transmissions and their interactions with polar components of the material.

Especially when the determination of water or moisture content is what is sought, the expression "quick" measurement technique has come to refer to those techniques in which the water or moisture content can be ascertained within a few seconds, compared to other conventional methods requiring substantially longer periods of time for their performance, e.g., methods involving drying ovens and operating on the basis of thermodynamic instead of electrical and electromagnetic principles.

It will be understood that it is already known to attempt to measure the concentration of such polar components in otherwise non-polar materials by measuring the attenuation of transmitted electromagnetic waves attributable to the dipole relaxation of the polar component. It is also known to combine such attenuation measurement with phase-difference or loss-angle measurements, in an attempt to correct for the effect upon the ultimate measurement signal of such factors as the density of the pourable bulk material involved, the thickness of the sample through which the electromagnetic waves are transmitted, the unevenness or irregularity of the boundary surfaces through which the transmitted electromagnetic waves enter and exit the sample, and so forth. In addition to such transmittance (attenuation) measuring techniques, it is also known to resort to reflection and resonance procedures. Also, besides the use of microwave waveguide technology to establish the requisite wave transmissions and dielectric interactions, it is of course even better known to employ more simple capacitive techniques for ascertaining the concentration of a polar component in an otherwise mainly non-polar material.

These various known techniques and approaches exhibit various already recognized disadvantages and limitations, and also certain disadvantages and limitations which will be seen to exist in comparison to the inventive technique to be described.

For example, when proceeding on a simple capacitive basis and utilizing the sample to be analyzed essentially as the dielectric layer for a more or less elementary capacitor structure, the frequency of the electromagnetic energy employed for the measurement cannot be freely increased without limit. Accordingly, it often becomes impossible to operate at frequencies high enough to preclude the onset of undesirable macropolarization phenomena; e.g., in the extreme case, the energy of the radiation employed may be, to an excessive fractional extent, wastefully and confusingly consumed in the work of merely effecting spatial separation of charged constituents of the material in the crude sense of electrostatics, and not be efficiently utilized for the main task of reorienting polar constituents. Also, with such more or less merely capacitive techniques, it is typically difficult to avoid physical and electrical engagement with the material to be analyzed.

When utilizing techniques based upon the reflection of electromagnetic waves, the measurement signal yielded by the technique tends to be mainly determined by wave reflection occurring at the boundary surface to the sample. As a result, it is mainly this part of the sample which interacts with or contributes to the measurement signal, whereas more deeply located parts of the sample tend not to appreciably participate in the interaction. Additionally, of course, the unevenness or irregularity of the sample's boundary surfaces has a very great influence upon the ultimate measurement signal.

When resort is had to resonance techniques, there arises mainly the problem that the size and amount of the sample is necessarily limited by the need to pack it into the limited space within the resonator chamber employed, and in the case of stray-field resonators it is furthermore typically very difficult to avoid physical and electrical engagement with the sample.

For these and other reasons, the conventional techniques which instead mainly rely upon the measurement of the attenuation of transmitted electromagnetic waves can be considered somewhat more advantageous. However, these too, as presently practiced, have their disadvantages:

1. When relying upon the measurement of transmitted-wave attenuation, the prior art has exhibited a consistent prejudice or commitment to the utilization of the frequency range in which the dipole relaxation of the polar components of interest in any particular measurement occur. To the extent that such prejudice is not merely a matter of habit, the usual view is that, in order to achieve a high signal-to-noise ratio in the ultimate measurement signal, the measurement frequency employed should be as close as possible to the maximum-relaxation-loss frequency $f_o = \frac{1}{2}\pi\tau$, $\tau$ being the dipole relaxation time of the polar component of interest in whatever specific material is being analyzed. The invention or concept behind such conventional choice of frequency is that the measurement signal be as much as possible dependent upon and affected by energy consumed in the work of irienting or reorienting polar constituents, i.e., so that the measurement signal obtained will be "tied in" as much as possible to the particular physical phenomenon upon which the concentration measurement is actually being based. Of course, when the measurement frequency employed is the maximum-relaxation-loss frequency $f_o$, i.e., is the reciprocal of the dipole-relaxation time-constant, the amount of power preferentially abstracted from the transmitted electromagnetic wave for the work of dipole orientation becomes great, resulting in a very high power loss, evidenced in a very great attenuation of the transmitted electromagnetic energy. However, because this very high power loss is so directly attributable to the polar component per se, it is generally considered positively desirable and essential. At the same time, because the resulting attenuation of the transmitted energy will be so very high, it is necessary, and therefore generally accepted without conscious dissatisfaction, that the thickness of the sample through which the radiation is transmitted be quite small, typically resulting in the use of a sample which is essentially merely a thin layer of material. Also, and as very well known, water and other polar components of constant interest for such measurements exhibit behaviour which is extremely dependent upon temperature, always necessitating that countermeasures of one type or another be resorted to in order to take such temperature-dependence into account.

2. When the measurement of transmitted-wave attenuation is supplemented by measurement of transmitted-wave delay or phase displacement, in an attempt to generate information which can be used to correct the attenuation measurement for factors such as sample thickness, density and so forth, this does not per se serve to eliminate the just explained shortcomings of the attenuation measurement per se. Also, when the material of interest is a pourable, mainly solid bulk material, such conventional approach presupposes a relatively high degree of uniformity of the size of the constituent particles, grains or chunks.

SUMMARY OF THE INVENTION

It is the general object of the invention to provide a quick measurement technique similar to the conventional phase-displacement technique, but so altered in its frequency-selection approach as to avoid, to a rather great extent, the disadvantages just explained. In particular, it is certainly a main object of the invention to provide such a technique in which the difficulties resulting from temperature-dependence are very greatly suppressed, to begin with. Also, it is an important object and advantage of the invention to provide a method which is not inherently limited to layer-thin samples but instead can equally well be applied to samples of very substantial thickness.

In accordance with the present invention, the concentration of polar components in a material otherwise mainly non-polar in character is accomplished by measuring the transmission delay of electromagnetic waves transmitted through a sample of such material, e.g., as expressed in units of time, as a phase displacement or a loss angle. However, the inventive technique departs from conventional techniques in the measuring-frequency range resorted to. With the material to be analyzed known, i.e., with its polar and non-polar components known, the measuring frequency employed is selected from a range having a lower limit and, somewhat more importantly for the purposes and advantages here contemplated, an upper limit. The lower limit of such frequency range is the lowest frequency at which signals can be both transmitted and detected using conventional microwave-technology structures, such as waveguides and the like. The upper limit of the frequency range to be employed is that frequency at which the dielectric constant of the polar components(s) of interest exceeds the dielectric constant of the non-polar and/or only negligibly polar remaining components of the material of interest; or alternatively, the upper frequency limit can be as high as the dipole-relaxation frequency $f_o$ for the case where $f_o$ would be lower than the alternative upper frequency limit just referred to. As already stated, the dipole-relaxation frequency $f_o = \frac{1}{2}\pi\tau$, $\tau$ being the dipole relaxation time-constant of the polar component of interest.

The frequencies to be employed will be further discussed below.

Roughly expressed, the technique of the present invention employs measuring frequencies considerably lower than hitherto employed for this type of technique. The lower limit of the frequency range from which the measuring frequency is to be selected in accordance with the present invention will merely be the lowest frequency reliably transmitted and especially detected using microwave-technology apparatuses, such as waveguides; at present, this lowest frequency is about 10 MHz. Of course, if the measuring frequency employed is selected from the lower part of such range, the frequency will be very much lower than anything resembling hitherto conventional practice, and it is accordingly the upper limit of the frequency range contemplated which most requires elucidation of its significance.

It will be understood that the dipole-relaxation frequency range of any given polar material is that frequency range at which and through which the electromagnetic energy transmitted through the material begins markedly to be consumed in the work of orienting or attempting to orient the polar molecules of the material. To either side of its dipole-relaxation frequency range, such a polar material does not comparably experience such an orienting effect. In general, the amount of energy drawn by the polar material for orientation reaches its maximum at the middle of the dipole-relaxation frequency range, which in general coincides with the maximum-relaxation-loss frequency $f_o$ per se, and, although marked in its effect to either side of the maximum-loss frequency $f_o$, decreases for frequencies proceeding away from $f_o$ in either direction therefrom. Accordingly, when operating, as is customarily done, as close as possible to the dipole-relaxation frequency $f_o$, there is not only a very great absorption of energy into the material, but furthermore a high degree of frequency-dependence in the amount of energy drawn for polar-molecule orientation work. In accordance with the underlying concept of the present invention, such conventional frequencies are positively to be avoided, first in order to reduce the amount of energy absorption hitherto considered positively desirable, and secondly to be able to work outside the range of marked frequency-dependence.

In principle, the reduction in both power attenuation and frequency-dependence here in question could also be achieved by going in the direction of higher than customary frequencies, i.e., going substantially higher than the customarily employed relaxation frequency $f_o$. However, it is presently preferred not to increase frequency in that direction, even when to do so would cause the dielectric constant of the non-polar components to become smaller than that of the polar component(s) by an even further increased amount.

One of the most characteristic features of the present invention, directly leading to one of its most characteristic advantages, is that the method is performed outside the frequency range associated with high levels of energy absorption attributable to polar-molecule orienting work. With similar techniques as conventionally employed, the energy absorption is intentionally so great as to limit the thickness of the sample that can be employed to layer-thin values, typically not more than about 0.2 meters, and in general to about 0.1 meter. In contrast, the technique of the present invention, among other things, permits the sample to be of substantial thickness, for example as thick as 1 meter, or even more. This is made possible by operating in a frequency range of low loss, and in general for a given material to be analyzed the frequency employed is selected lower and lower as the thickness of the sample to be dealt with is greater and greater. For example, one particularly important practical application of the present invention relates to the measurement of the moisture content of thick masonry walls. In general, however, the techniques of the present invention can equally well be practiced upon solid, liquid or gaseous materials and can be performed without physical or electrical engagement of the material of interest.

When practicing the present invention, the frequency employed should not exceed a maximum value following logically from the thickness of the sample to be employed and the reasonably expected maximum concentration of the polar component(s) of interest. Because, in accordance with the present invention, one is to begin with operating at frequencies below $f_o$, if one is presented with a sample of greater than usual thickness, and therefore presented with an unacceptably great attenuation in the transmitted-wave power, one can merely shift down to lower and lower measuring frequencies, to reduce the per-unit-thickness attenuation until the total attentuation for the thicker than usual sample is confined to the values customarily leading to the use of, for example, 0.1-meter-thick samples.

According to a further concept of the invention, when the material of interest is of heterogeneous physical structure, the measuring frequency employed should be above the upper limit of the relaxation-frequency range of macropolarization effects attributable to the presence of free charge carriers in the material. Materials of heterogeneous physical structure is herein intended to refer to materials which exhibit physical boundary surfaces internal to the external or outermost boundary surfaces of the sample as a whole, for example as will evidently be the case when the material of interest is a pourable granular solid and each grain thereof has a boundary surface of its own. To the extent that at least one constituent component of such a heterogenous material is electrically conductive, surface charge can accumulate on the internal boundary surfaces, and this free surface charge can participate in macropolarization effects, e.g., can draw energy from the transmitted radiation in order to conductively displace itself in a sense effecting spatial separation of surface charge on the surface of such constituent granules or the like. Such surface-charge macropolarization effects lead to a very considerable increase in the dielectric constant of the sample as a whole, and constitute a phenomenon contaminating the purity of the information which the ultimate measurement signal is to contain. For situations such as these, it is a further concept of the invention not merely to operate at a frequency substantially below the normally employed dipole-relaxation frequency $f_o$, but furthermore to operate at a frequency which is above the macropolarization relaxation-frequency range. One example of such free charge carriers are dissolved salts.

As already indicated, the inventive method employs the technique of measuring the time delay or phase displacement of the electromagnetic radiation transmitted through the sample. If the phase displacement resulting with a particular sample exceeds 360°, then that component of the total phase displacement which is 360° or an integral multiple thereof can, in accordance with the present invention, be determined in any of the following ways:

a. Use can be made of two different measuring frequencies, preferably with both selected in accordance with the present invention, the two frequencies both being frequencies for which the dielectric constant of the material of the sample will be the same, i.e., in the range of relatively low frequencies at which the effects of dipole relaxation will negligibly make themselves felt in the overall dielectric constant of the material of the sample.

b. Alternatively, samples of two different thicknesses can be employed to ascertain what integral multiple of 360° (including 360° itself) is involved.

c. Alternatively, attenuation measurements can be performed, in order to ascertain merely the order of magnitude of the total phase displacement involved.

These alternative expedients need only be resorted to, however, when the concentration of the polar component of interest fluctuates within a wide range of variation. It is not necessary to each time thusly ascertain what integral multiple of 360° is contained in the sample's total phase displacement, in those situations where the actual concentration of the polar component of interest is certain to fall within a limited range of variation, for example when the measurement technique of the present invention is used merely to measure deviations from nominal concentration values in quality-control applications for mass-production contexts.

The advantages inherent in the inventive technique become of particular practical significance when the polar component of the material to be analyzed is water and the non-polar or negligibly polar components are solids. An especially important instance of such a material would, for example, be coal. When the water content in otherwise solid material is to be ascertained, then in accordance with a further concept of the invention it is particularly preferred to measure the time delay of the electromagnetic waves transmitted through the material of interest utilizing frequencies between 1 and 25 GHz, preferably between 2 and 8 GHz. Then, the amount of water present, measured by ratio of weight of water to weight of sample containing the water, is advantageously determined by measuring the weight of the sample and normalizing the measured weight of the sample with respect to the surface area of the sample penetrated by the electromagnetic radiation.

By adopting this approach with regard to materials which are solids in pourable form, it becomes possible to dispense with separate determination of the effects of the density of the material per se and of the grain or particle size of the material.

In order to determine the relative water content by weight (weight of water divided by weight of the sample containing the water), it suffices to weigh the sample, i.e., when this is feasible, because the construction of the measuring apparatus employed, e.g., a waveguide accommodating the sample, is of course known in advance, with the surface area penetrated by the transmitted radiation therefore likewise known in advance. If weighing of the sample is not possible, e.g., in the case of an erected masonry wall whose water content is to be measured, then it suffices to know the thickness of the sample, with the density of the material of the sample being separately determined by whatever means is most convenient for the situation involved.

A very important advantage of the inventive technique is the great extent to which the effect of temperature variations is suppressed in the ultimate measurement signal produced, especially when in accordance with a preferred concept of the invention the measuring fequency employed is no greater than at the lower limit of the dipole-relaxation frequency range of the polar component involved. The degree to which the inventive technique is temperature-independent in its very nature is unprecedented in the art, it having been hitherto impossible or at best extremely difficult to achieve anything resembling actual temperature-independence.

We have established that to achieve any substantial degree of temperature-independence, it is necessary that the measuring frequency employed be between 0.05 $f_o$ and 0.9 $f_0$, $f_0$ being as already stated the dipole-relaxation frequency of the polar component whose concentration is to be determined and being equal to $\frac{1}{2}\pi\tau$, wherein $\tau$ is the dipole-relaxation time-constant of the polar component of interest. The relaxation time-constant $\tau$ of the dipole relaxation of a polar substance, it will be understood, is a value which is in general different for each individual polar substance. Our experience has indicated, furthermore, that to achieve really optimal temperature-independence, the measuring frequency employed should be between 0.1 $f_o$ and 0.5 $f_o$.

The time delay which electromagnetic waves of any given frequency experience in passing through a material, i.e., compared to their passage through the same volume of free space, can of course be determined either by measuring per se the travel time of a very short packet of electromagnetic waves (i.e., real-time measurement) or else indirectly by monitoring, for example, the phase shift which such waves assume in passing through the substance of interest. The latter technique is often, but by no means exclusively, employed when instead of a single measuring frequency a limited continuous range of frequencies are transmitted through the substance of interest simultaneously, in which event the middle frequency within such continuous range of simultaneously employed frequencies would constitute the measuring frequency in the sense of the present invention.

EXAMPLES

If, for example, the polar component of interest is water, then, as already stated, the frequency range from which the measuring frequency is to be selected, to minimize temperature-dependence, should be between about 2 and 8 gigahertz. For the purposes of explanation, and in particular to illustrate the remarkable temperature-independence of the inventive technique, an example will be given in which it is desired to ascertain the water content in fine-grained coal, measuring the delay time of the transmitted radiation by measuring the phase shift assumed by the radiation. The measuring apparatus employed was constituted by a sweep generator type 430 A manufactured by the Weinschel Engineering Company of Gaithesburg, Md., and a network analyzer of types 8410A, 8411A, 8413A, 4743A of the Hewlett-Packard Company of Palo Alto, Calif. The samples of coal to be investigated were accommodated in hollow-conductor waveguides of rectangular cross-section. A variety of such waveguides, of different respective dimensions, can be kept on hand so as to be able to work at any particular frequency desired, with the selected waveguide being connected to the network analyzer via conventional adapters. The samples were packed into the rectangular-cross-section waveguides in such a manner that, for a length d of the hollow-conductor waveguide, the entire interior cross-sectional area A of the waveguide was completely and neatly filled with the sample. By measuring the transmitted radiation both with and without the sample thusly accommodated in the waveguide, the phase shift attributable to the presence of the sample, expressed in degrees, was ascertained, and for comparison the attenuation or damping D expressed in dB. Inasmuch as the phase angle $\zeta$ is indicatable only in the range from $-180°$ to $+180°$, the total phase-shift angle $\phi$ is undetermined by an integral multiple of 360° (including 360° itself). However, inasmuch as the propogation velocity of the electromagnetic waves is reduced during travel through the sample, the total phase-shift angle $\phi$ will be negative, i.e., $$\phi = -n \cdot 360° + \zeta.$$

The value of n can be ascertained, for example, by performing two otherwise similar measurements upon two samples of differing length or thickness d, inasmuch as the phase angle will be proportional to d. To cancel out the factors of density of the pourable material and thickness of the sample employed, the time delay, which is proportional to the measured phase shift, and also the attenuation were both normalized with respect to the weight G of the sample per unit surface area A. I.e., the relative time-delay interval was measured as $$t_{rel} = -(1000/360) \cdot (\phi/f) \cdot (A/G)$$

with $t_{rel}$ being expressed in units of picosecond-cm² per gram; with $\phi$ being expressed in degrees; with f being expressed in gigahertz; with A being expressed in squarecentimeters; with G being expressed in grams. Likewise, the relative attenuation or damping was ascertained as $$D_{rel} = D \cdot (A/G)$$

with $D_{rel}$ being expressed in units of decible-cm² per gram; and with D expressed in dB.

Table 1 below tabulates the result of the inventive determination of relative time delay, here by measuring the phase shift through moist, fine-grained coal (grain size range 1–0 mm), using a hollow-conductor waveguide meeting I.E.C. norm R 48 and accordingly adapted for the frequency range 3.95–5.8 gigahertz, with the waveguide accommodating a packed-in sample of such coal, and with the measuring frequency employed having been 4 gigahertz for optimal reduction of temperature-dependent effects. For comparison purposes, attenuation measurements were performed at the upper boundary surface of the hollow-conductor waveguie utilizing a measuring frequency of 5.8 gigahertz. The measurements were first performed at room temperature (22° C.) and thereafter repeated after the sample was cooled down to a temperature of 6.5° C. The water content (w/%) of the coal, determined in advance, was varied between 4 and 30%, expressed in terms of the weight of water in the sample divided by the total weight of the sample.

TABLE 1

| W/% | $t_{rel}$/ps $\frac{cm^2}{g}$ ; 4 GHz | | | $D_{rel}$/dB $\frac{cm^2}{g}$ ; 5,8GHz | | |
|---|---|---|---|---|---|---|
| | 6,5° C. | 22° C. | Δ W | 6,5° C. | 22° C. | ΔW |
| 4,1 | 37,37 | 37,76 | | 0,5734 | 0,5247 | ±0,3% |
| 10,7 | 49,28 | 49,55 | | 1,4351 | 1,1326 | ±1,4% |
| 16,3 | 60,69 | 60,83 | ±0,1% | 2,2339 | 1,7357 | ±2,1% |
| 22,9 | 73,96 | 73,53 | | 3,4211 | 2,4471 | ±2,2% |
| 29,3 | 89,22 | 89,76 | | 5,3749 | 3,9588 | ±2,39% |

As Table 1 indicates, utilizing a measuring frequency of 4 gigahertz, the relative time delay was virtually temperature-independent. Thus, the error in the inventive measurement of water content W, attributable to temperature variations, was on the order of ±0.1% throughout the entire range of variation of water content considered. In contrast, the attempt to ascertain water content by reliance upon the relative attenuation $D_{rel}$ exhibited an error due to temperature change which climbed up to 2.4% as greater and greater water content was involved.

Table 2 demonstrates tests performed merely to show that a sizable error attributable to temperature-dependence does not affect a water-content measurement based upon relative time delay, if the measuring frequency has been chosen outside or even near the limit of the optimal range.

TABLE 2

| W/% | $t_{rel}$/ps $\frac{cm^2}{g}$ ; 8 GHz | | |
|---|---|---|---|
| | 6,5° C. | 22° C. | Δ W |
| 4,1 | 30,45 | 31,21 | ±0,2% |
| 10,7 | 40,23 | 41,2 | ±0,3% |
| 16,3 | 50,63 | 51,96 | ±0,4% |
| 22,9 | 62,67 | 64,36 | ±0.5% |
| 29,3 | 77,98 | 81,05 | ±0,5% |

In demonstration tabulated in Table 2, a measuring frequency of 8 gigahertz, not in accordance with the present invention, was employed. In other respects the set-up and procedure were identical to that tabulated in the left half of Table 1, except that, in order to be able to use this non-inventive 8 GHz measuring frequency, it was necessary to instead use a hollow-conductor waveguide meeting I.E.C. norm R 70, i.e., adapted for a frequency range of 5.8–8.2 GHz.

The duration of the measuring operation per se, including also evaluation of the resultant measurement signal utilizing a computer, amounted to a mere 0.2 seconds for each of the tabulated measurements. However, the weighing of the samples and the packing of the sample into the interior of the waveguide required about 1–2 minutes; in applications where the use of automated equipment for the weighing and packing would be justified, it would of course be possible to perform this preliminary work in a much shorter time. Likewise, the inconvenience of having to pack a hollow waveguide with the sample could be bypassed by resorting to a contact-free structure such as a horn antenna.

The tests tabulated above are merely exemplary of a very great number and variety which we have performed. The results, i.e., the temperature-independence in particular, were equally outstanding at still higher temperatures, for coal of other grain sizes, and for a great variety of polar components and non-polar or negligibly polar components.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a method of ascertaining the concentration of a polar component of an otherwise non-polar or negligibly polar material, the step of using a microwave waveguide to transmit electromagnetic waves through a sample of the material and measuring the transmission delay of the thusly transmitted electromagnetic waves, the frequency of the electromagnetic waves not exceeding a predetermined upper limit, the upper limit being the lower one of two frequencies, one frequency being the frequency at which the dielectric constant of the polar component exceeds that of the remaining, non-polar or negligibly polar component of the material, the other frequency being the dipole-relaxation frequency $f_o$ of the polar component, wherein $f_o = \frac{1}{2}\pi\tau, \tau$ being the dipole-relaxation time-constant of the polar component.

2. In a method as defined in claim 1, the measurement of the transmission delay comprising measuring the phase shift experienced by the electromagnetic waves transmitted through the sample.

3. In a method as defined in claim 1, the material being of heterogeneous physical structure comprising physical constituents having boundary surfaces of their own, whereby any sample of such material will have internal boundary surfaces interiorly of its outermost or exterior boundary surface, the frequency of the electromagnetic waves employed furthermore being higher than the macropolarization relaxation-frequency range of the free charge within such material.

4. In a method as defined in claim 1, the frequency of the electromagnetic waves employed being no higher than at the lower limit of the dipole-relaxation frequency range of the polar component.

5. In a method as defined in claim 4, the frequency of the electromagnetic waves employed being between $0.05f_o$ and $0.9f_o$.

6. In a method as defined in claim 5, the frequency of the electromagnetic waves employed being between $0.1f_o$ and $0.5f_o$.

7. In a method as defined in claim 2, the phase shift being greater than 360°, the measurement of the phase shift including ascertaining what integral multiple of 360° is contained in the phase shift by performing the steps of claim 1 twice using two different frequencies at both of which the material has the same overall dielectric constant.

8. In a method as defined in claim 2, the phase shift being greater than 360°, the measurement of the phase shift including ascertaining what integral multiple of 360° is contained in the phase shift by performing the steps of claim 1 twice, each time using a sample of the material having a different respective thickness as measured in the direction in which the electromagnetic waves propagate.

9. In a method as defined in claim 2, the phase shift being greater than 360°, the measurement of the phase shift including ascertaining what integral multiple of 360° is contained in the phase shift by furthermore measuring the attenuation experienced by the electromagnetic waves transmitted through the sample and ascertaining therefrom the order of magnitude of the phase shift.

10. In a method as defined in claim 1, the material being a solid and the polar component being the water in the material, the frequency employed being between 1 and 25 GHz.

11. In a method as defined in claim 10, the material being coal.

12. In a method as defined in claim 10, the frequency employed being between 2 and 8 GHz.

13. In a method as defined in claim 12, the material being coal.

14. In a method as defined in claim 1, transmitting the electromagnetic waves through a sample of the material having a predetermined thickness as measured in the direction of wave propagation, the frequency employed for the electromagnetic waves not exceeding a predetermined frequency dictated in conjunction by the thickness of the sample and the highest concentration value expected to be encountered.

15. In a method as defined in claim 1, transmitting the electromagnetic waves through a sample of the material having a predetermined thickness as measured in the direction of wave propagation, then increasing the thickness of the sample and decreasing the frequency employed.

16. In a method as defined in claim 1, transmitting the electromagnetic waves through a sample of the material having a predetermined thickness as measured in the direction of wave propagation, then decreasing the thickness of the sample and increasing the frequency employed.

* * * * *